United States Patent
Kucklick et al.

(10) Patent No.: US 7,500,947 B2
(45) Date of Patent: Mar. 10, 2009

(54) ATRAUMATIC ARTHROSCOPIC INSTRUMENT SHEATH

(75) Inventors: Theodore R. Kucklick, Los Gatos, CA (US); Martin Trieb, San Jose, CA (US)

(73) Assignee: Cannonflow, Inc., San Jose, CA (US)

( * ) Notice: Subject to any disclaimer, the term of this patent is extended or adjusted under 35 U.S.C. 154(b) by 569 days.

(21) Appl. No.: 11/094,626

(22) Filed: Mar. 29, 2005

(65) Prior Publication Data
US 2005/0234298 A1 Oct. 20, 2005

Related U.S. Application Data

(63) Continuation-in-part of application No. 11/016,274, filed on Dec. 17, 2004, now Pat. No. 7,435,214, which is a continuation-in-part of application No. 10/769,629, filed on Jan. 29, 2004, now Pat. No. 7,413,542.

(51) Int. Cl.
*A61B 1/015* (2006.01)

(52) U.S. Cl. .................. 600/114; 600/156; 600/128; 604/164.02

(58) Field of Classification Search ............ 600/114, 600/128, 153, 156, 130; 604/164.02
See application file for complete search history.

(56) References Cited

U.S. PATENT DOCUMENTS

| | | | | |
|---|---|---|---|---|
| 4,491,132 | A | | 1/1985 | Aikins .................. 128/305 |
| 4,646,722 | A | | 3/1987 | Silverstein et al. ........... 128/4 |
| 4,674,500 | A | | 6/1987 | DeSatnick .............. 128/305 |
| 4,717,379 | A | * | 1/1988 | Ekholmer .............. 604/43 |
| 4,721,097 | A | | 1/1988 | D'Amelio ............... 128/4 |
| 4,820,265 | A | | 4/1989 | DeSatnick et al. |
| 4,886,049 | A | | 12/1989 | Darras et al. ............. 128/4 |
| 4,897,079 | A | | 1/1990 | Zaleski et al. ............ 604/22 |
| 4,973,321 | A | | 11/1990 | Michelson |
| 5,037,386 | A | * | 8/1991 | Marcus et al. ............ 604/43 |
| 5,179,935 | A | * | 1/1993 | Miyagi ................. 600/142 |
| 5,184,602 | A | | 2/1993 | Anapliotis et al. .......... 128/6 |
| 5,273,545 | A | | 12/1993 | Hunt et al. ............. 604/197 |
| 5,290,279 | A | | 3/1994 | Bonati et al. |
| 5,337,734 | A | | 8/1994 | Saab ................... 128/4 |
| 5,386,817 | A | | 2/1995 | Jones ................. 600/104 |
| 5,413,092 | A | | 5/1995 | Williams, III et al. ........ 128/4 |
| 5,415,157 | A | | 5/1995 | Welcome .............. 600/121 |
| 5,449,356 | A | * | 9/1995 | Walbrink et al. ........... 606/49 |
| 5,483,951 | A | | 1/1996 | Frassica et al. .......... 600/104 |
| 5,527,276 | A | | 6/1996 | Bruce .................. 604/54 |
| 5,571,128 | A | | 11/1996 | Shapiro ................ 606/167 |
| 5,575,753 | A | | 11/1996 | Yabe et al. ............. 600/123 |
| 5,575,756 | A | * | 11/1996 | Karasawa et al. ......... 600/157 |
| 5,593,394 | A | * | 1/1997 | Kanesaka et al. ......... 604/524 |
| 5,601,603 | A | * | 2/1997 | Illi ................... 606/213 |

(Continued)

*Primary Examiner*—John P Leubecker
(74) *Attorney, Agent, or Firm*—Susan L. Crockett, Esq.; Crockett & Crockett

(57) ABSTRACT

An arthroscopic inflow and outflow sheath providing an improved inflow and outflow system reducing the diameter of a continuous flow system while providing fluid management during arthroscopy. The improved arthroscopic inflow and outflow sheath comprises an elongated atraumatic sheath having an inner surface, outer surface, proximal end, and distal end. The atraumatic sheath further comprises plurality of ribs or webs extending from the inner surface of the sheath and designed to contact an outer surface of the arthroscope thereby creating outer lumens facilitating the inflow and outflow of fluid to a surgical site.

19 Claims, 8 Drawing Sheets

U.S. PATENT DOCUMENTS

| | | |
|---|---|---|
| 5,637,075 A * | 6/1997 | Kikawada .................. 600/153 |
| 5,762,604 A | 6/1998 | Kieturakis .................. 600/115 |
| 5,797,882 A * | 8/1998 | Purdy et al. ............ 604/164.09 |
| 5,800,409 A | 9/1998 | Bruce ......................... 604/280 |
| 5,924,977 A | 7/1999 | Yabe et al. |
| 5,947,990 A | 9/1999 | Smith ......................... 606/180 |
| 5,989,183 A | 11/1999 | Reisdorf et al. ............. 600/156 |
| 6,086,542 A | 7/2000 | Glowa et al. ................ 600/561 |
| 6,110,103 A | 8/2000 | Donofrio .................... 600/121 |
| 6,126,592 A | 10/2000 | Proch et al. ................. 600/114 |
| 6,174,280 B1 | 1/2001 | Oneda ........................ 600/121 |
| 6,203,537 B1 | 3/2001 | Adrian |
| 6,269,340 B1 | 7/2001 | Ford et al. |
| 6,293,909 B1 | 9/2001 | Chu et al. ................... 600/121 |
| 6,315,714 B1 | 11/2001 | Akiba ........................ 600/114 |
| 6,447,446 B1 | 9/2002 | Smith et al. ................ 600/157 |
| 6,558,379 B1 | 5/2003 | Batchelor et al. ............ 606/41 |
| 6,692,431 B2 | 2/2004 | Kazakevich .................. 600/178 |
| 6,827,710 B1 * | 12/2004 | Mooney et al. ............. 604/500 |
| 6,878,149 B2 * | 4/2005 | Gatto .......................... 606/46 |
| 2001/0056222 A1 * | 12/2001 | Rudischhauser et al. .... 600/130 |
| 2002/0173699 A1 | 11/2002 | Becker et al. ............... 600/114 |
| 2003/0004400 A1 * | 1/2003 | Smith ......................... 600/153 |
| 2003/0018340 A1 | 1/2003 | Branch ........................ 606/96 |
| 2004/0082915 A1 * | 4/2004 | Kadan .................. 604/164.04 |
| 2005/0043690 A1 | 2/2005 | Todd .......................... 604/248 |
| 2005/0085695 A1 * | 4/2005 | Shener et al. ............... 600/156 |
| 2006/0041186 A1 * | 2/2006 | Vancaillie ................... 600/128 |

* cited by examiner

ATRAUMATIC ARTHROSCOPIC INSTRUMENT SHEATH

This application is a continuation-in-part of U.S. application Ser. No. 11/016,274 filed Dec. 17, 2004, now U.S. Pat. No. 7,435,214, which is a continuation-in-part of U.S. application Ser. No. 10/769,629 filed Jan. 29, 2004 now U.S. Pat. No. 7,413,542.

FIELD OF THE INVENTIONS

The inventions described below relate to the field of arthroscopic surgical instruments.

BACKGROUND OF THE INVENTIONS

Medical science has long sought ways to minimize the dangers and trauma inherent in invasive surgical procedures. To this end, surgical techniques and instruments have been developed which, among other things, reduce the size and number of the incisions required to perform various surgical procedures. These techniques and instruments have been remarkably successful. Procedures that only a few years ago would require multiple incisions several inches in length are today being performed with just a few small incisions.

During minimally invasive surgeries, surgical instruments such as trocars, cannulas, and optical medical devices, including endoscopes, cystoscopes, arthroscopes, laparoscopes, etc., are inserted through small incisions or portals in a patient's body or body cavity and manipulated to perform surgical procedures within the patient.

Minimally invasive surgical procedures such as arthroscopy are safer than open surgery and result in quicker patient recovery, shorter hospital stays, and lower health care costs. Accordingly, minimizing invasiveness continues to be of importance, and there is a continuing need for devices and methods that achieve this objective.

One significant barrier to further minimizing the invasiveness of surgery is the necessity of many surgical instruments to have fluid channels. These channels effectively add to the outer diameter of the instruments. For example, known endoscopic instruments provide inflow/outflow through an assembly of concentric sheaths that define channels for inflow and outflow of fluids to and from the operative or surgical site. The fluid may be an irrigating solution that helps maintain a clear view of the site for the physician. Certain known irrigating systems provide simultaneous and continuous inflow and outflow. These systems are known as "continuous flow" systems.

The known inflow and outflow endoscope systems introduce an irrigating fluid into the surgical site. For this purpose, the endoscope has an inflow channel defined by the inner surface of the sheath. The fluid passes through the channel and exits the distal end of the sheath to irrigate the operative site. Fluid at the surgical site may be withdrawn through an outflow channel defined by the outer surface of the inner sheath and the inner surface of a surrounding outer sheath. The outflow channel originates at the distal end (front end) of the instrument and transports fluid to an exit point at the proximal end of the outer sheath. The diameter of these systems requires larger surgical portals.

Another barrier to minimally invasive surgery is fluid management within the surgical site. During arthroscopy, fluid is pumped into the joint under pressure to maintain distention in the joint for visualization and hemostasis. A computerized pump that precisely monitors the flow rate and intra-articular pressure usually accomplishes this. Poor fluid management, however, can lead to complications. If pressure is set too low, excessive bleeding and poor visualization could occur. If the pressure is set too high and for too long, significant swelling in the surrounding tissue can occur. During arthroscopic knee surgery, excessively high pressure could result in compartment syndrome of the leg.

In arthroscopic surgery, as well as other surgical procedures, there remains a significant need for improved techniques that reduce the size of the portals while providing substantially continuous and properly managed fluid inflow and outflow. The Applicant's improved inflow/outflow sheath reduces the diameter of the continuous flow system while properly managing surgical site fluid inflow and outflow.

SUMMARY

The devices and methods shown below provide for smaller surgical portals during arthroscopy while also providing the management of substantially simultaneous inflow and outflow of fluid to the surgical site. The atraumatic inflow/outflow sheath allows a surgeon to drain fluids from or introduce fluids into the surgical field, thereby keeping the surgical field clear. The inflow/outflow sheath is a tube having inwardly extending ribs that form multiple lumens when the arthroscope is inserted. The proximal portion of the sheath is provided with fluid ports, a manifold and other means of controlling the flow of fluid inside the sheath. The distal portion of the inflow/outflow sheath is provided with a plurality of holes. The distal tip of the atraumatic inflow/outflow sheath is frustoconical in shape allowing a seal to be formed between the sheath and the outer surface of a surgical instrument when an instrument is inserted into the sheath and extends distally past the distal tip of the sheath. Each hole communicates with one or more of the lumens inside the tube, thereby allowing fluid to flow between the surgical field and sources or sinks located outside the patient. The inflow/outflow sheath thereby allows the surgeon to maintain a clear surgical field and protect the patient from accidental injury while eliminating the need for a third irrigation instrument.

The atraumatic inflow/outflow sheath may be provided with a working channel to enable access of additional surgical instruments to a surgical site through the sheath. The sheath may also be provided with pressure ports facilitating pressure measurements to be taken from the surgical site. These measurements are used to manage the inflow and outflow of fluids to the surgical site. The sheath may also be provided with illumination ports for illuminating the surgical site in order to enhance imaging during surgery.

DETAILED DESCRIPTION OF THE INVENTIONS

Figure 1:
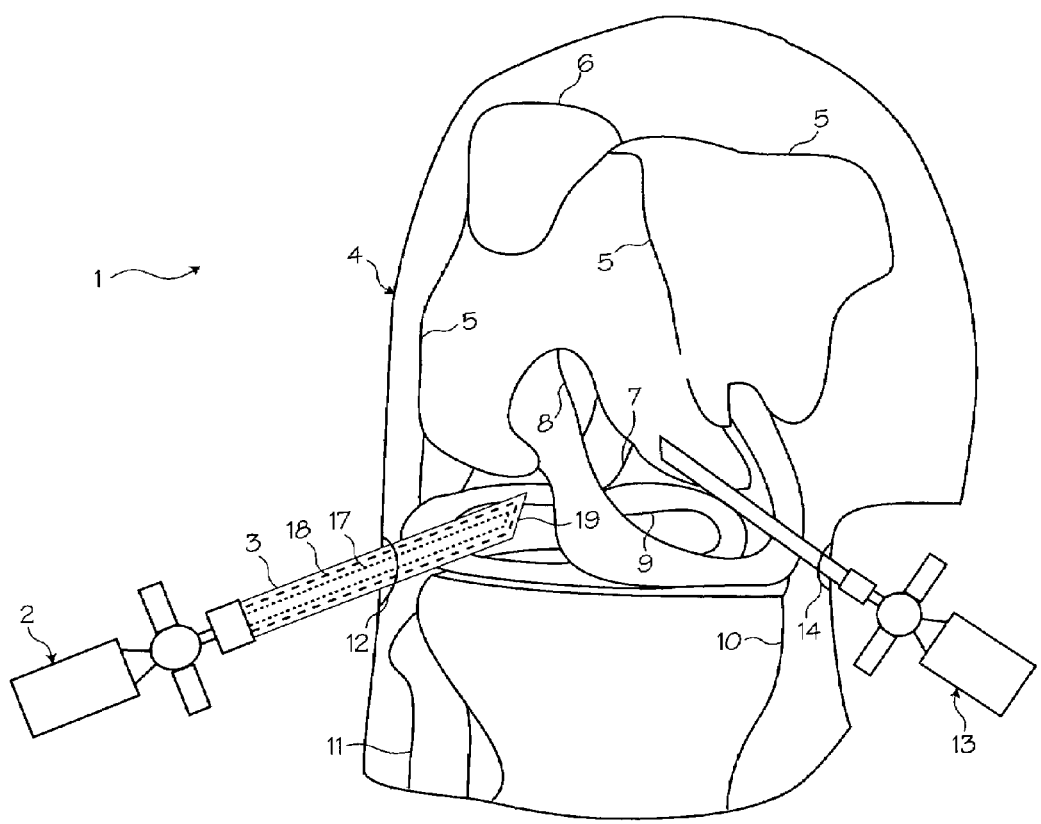
FIG. 1 shows a method of performing arthroscopic surgery on a patient.

FIG. 1 shows a method of performing arthroscopic surgery on a patient 1 by using an arthroscopic instrument such as an arthroscope 2 sheathed in an atraumatic sheath 3. An arthroscopic instrument may be an arthroscope, endoscope, awl, pick, shaver, etc. In FIG. 1, the various parts of the arthroscope are shown in phantom to indicate their positions inside the sheath. Various anatomical landmarks in the patient's knee 4 are shown for reference, including the femur 5, patella 6, posterior cruciate ligament 7, anterior cruciate ligament 8, meniscus 9, tibia 10 and fibula 11. During surgery, the surgeon introduces the arthroscope 2 into the knee via a first incision 12 in order to visualize the surgical field. A trimming instrument 13 is introduced through a second incision 14 to remove or trim tissue that the surgeon determines should be removed or trimmed. Optionally, an irrigating instrument may be introduced through a third incision in order to irrigate the surgical field and thereby maintain a clear view. As discussed below, the irrigating instrument may be replaced by a combined arthroscope and inflow/outflow atraumatic sheath.

The arthroscope 2 is an optical instrument surrounded by a rigid cannula 17 having a distal edge that typically is cut at an angle. To protect the patient from unintended injury or trauma during the procedure, the arthroscope has been inserted into a resilient, outer introducer sheath or atraumatic sheath 3 that extends over the rigid cannula.

Figure 2:
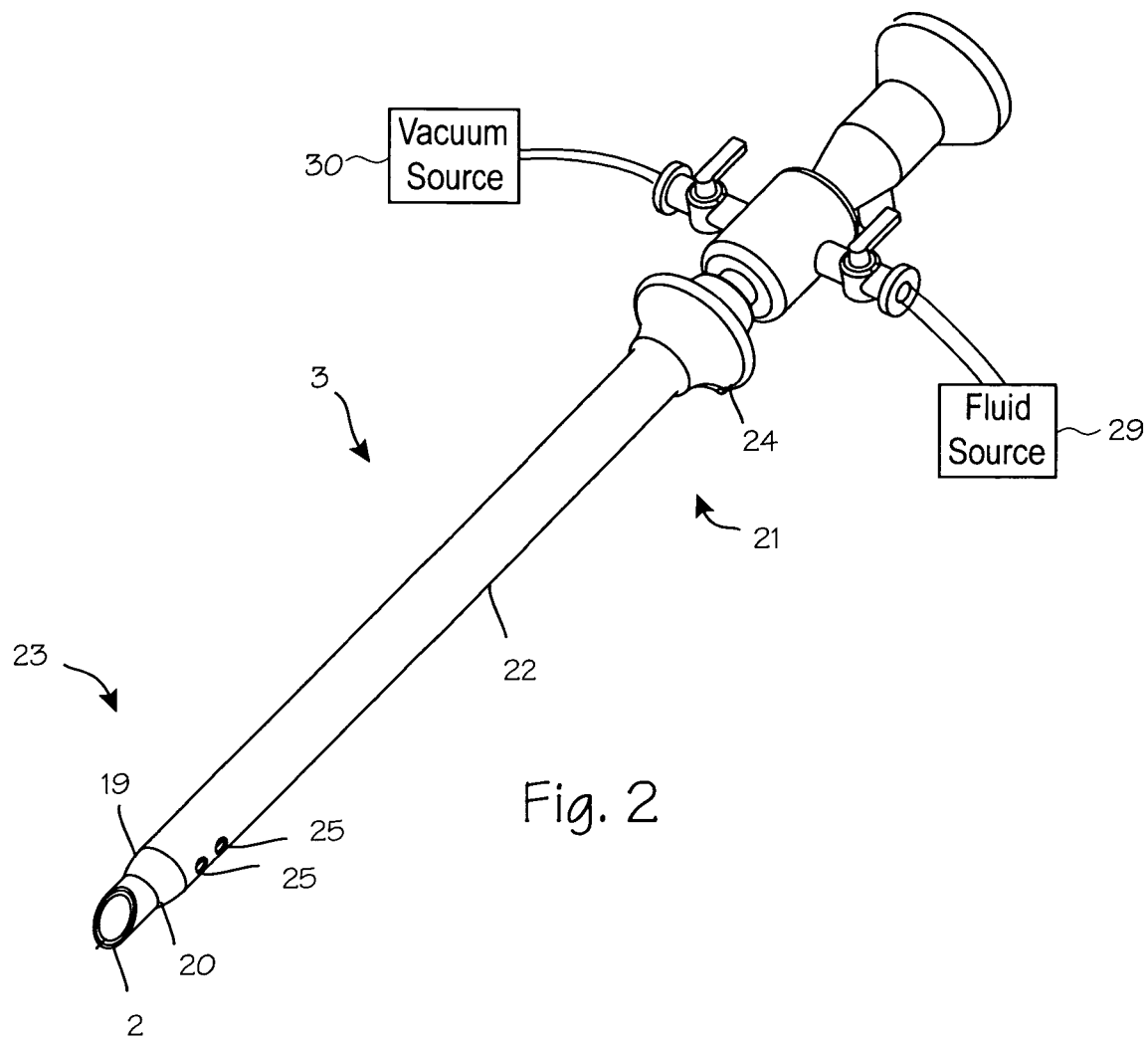
FIG. 2 shows an inflow/outflow atraumatic sheath for use with arthroscopic instruments.

FIG. 2 illustrates the inflow/outflow atraumatic sheath 3. The atraumatic sheath 3 is a tube 22 with of a resilient material, such as a sterilizable polymer like soft plastic or rubber, characterized by a central lumen. The inner diameter of the atraumatic sheath is sized and dimensioned to closely fit over the outer diameter of an arthroscopic instrument 2. The tube 22 is characterized by a distal section 23 having a distal tip 19 and a proximal section. The distal tip of the atraumatic sheath is provided with a frustoconcial shape and an opening 20 that is slightly smaller in diameter than the outer diameter of the distal tip of the arthroscope and/or the rigid cannula or other surgical instrument. Alternatively, the tip may have an arcuate cross-section. The opening 20 is provided in the atraumatic sheath so the surgeon may insert the endoscope 2, or other surgical instruments, through the opening and into the surgical space. The distal section 23 of the sheath further comprises holes 25 or other openings that may be placed in fluid communication with a fluid source or vacuum source. The proximal section 21 of the atraumatic sheath is provided with a hub 24 manufactured from an elastomer to allow medical personnel to easily pull the atraumatic sheath over and secure the sheath to the rigid cannula, arthroscope 2 and/or arthroscopic instrument. Further, the hub 24 can be adapted for coupling to a fluid source 29 and/or a vacuum source 30. The proximal section 21 of the atraumatic sheath may also be provided with fittings, such as a locking hub or snap latches, that attach to fittings or openings disposed on the arthroscope or other instrument, thereby securing the atraumatic sheath.

The outer surface of the atraumatic sheath 3 may be provided with a smooth coating to allow the arthroscope and rigid cannula to more easily move within an operating site. For example, the sheath may be provided with a Teflon® (PTFE or expanded polytetrafluoroethylene) coating or covered with a water-activated lubricant. In contrast, the inner surface of the atraumatic sheath (the walls that define the lumen of the tube) may be provided with a non-slip coating or other high coefficient of friction coating. For example, the inner surface of the atraumatic sheath may be coated with a co-extruded tacky thermoplastic elastomer (TPE). The non-slip coating prevents the sheath from easily slipping over the outer surface of the rigid cannula or arthroscope, thereby helping to prevent the atraumatic sheath from twisting or slipping around the arthroscope.

Figures 3, 4:
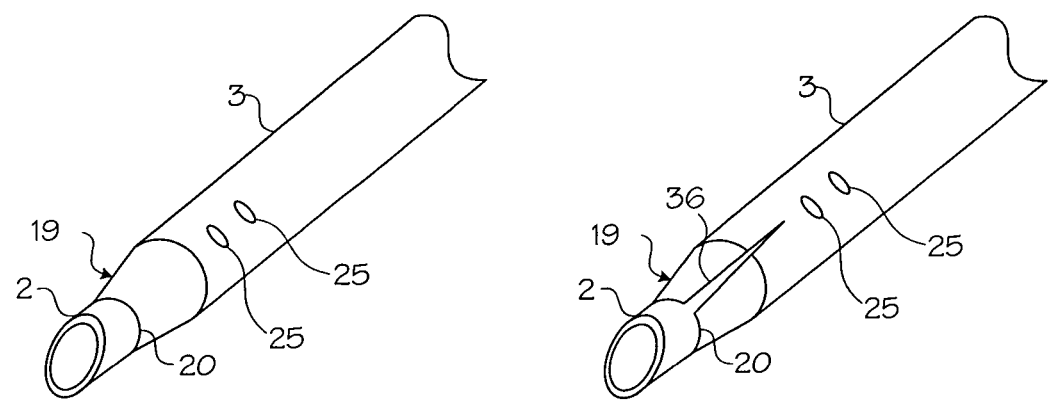
FIG. 3 shows the distal portion of an atraumatic sheath and an arthroscope extending distally from the distal end of the sheath.
FIG. 4 shows the distal portion of an atraumatic sheath and an arthroscope extending distally from the distal end of the sheath.

FIGS. 3 and 4 show the distal section 23 of an inflow/outflow atraumatic sheath 3 and an arthroscope 2 extending distally from the distal tip 23 of the sheath 3. The arthroscope may then be extended distally out of the opening 20 and the surgical space visualized. FIG. 3 shows the distal portion of an atraumatic sheath and an arthroscope extending distally from the distal end of the sheath 3. Holes 25 are provided in the distal portion of the sheath. The holes 25 communicate with one or more lumens in the sheath. The lumen or lumens communicate with a vacuum source, fluid source, therapeutic agent source or a combination of sources. Thus, the holes 25 provide for the inflow and outflow of fluids during a procedure.

The tube 22 of the sheath and the distal tip 23 are manufactured from the same flexible sterilizable polymer. Alternatively, the distal tip 23 of the inflow/outflow atraumatic sheath can be made of an elastic material having a higher modulus of elasticity than the modulus of elasticity found in the material of the proximal portion of the sheath. The distal tip of the sheath has an inner diameter that is slightly smaller than the outer diameter of most arthroscopes.

When the sheath 3 is in use, a user inserts the arthroscope into the sheath 3. The distal tip expands 23 as the distal end of the arthroscope 2 slides past the distal tip of the sheath. Because the inner diameter of the tip 23 is less than the outer diameter of the arthroscope 2, the tip will form a seal with the outer surface of the arthroscope 2.

FIG. 4 shows the distal portion of an atraumatic sheath 3 and an arthroscope 2 extending distally from the distal tip 23 of the sheath. Holes 25 are provided in the sheath to allow the inflow and outflow of fluids during a surgical procedure. A slit 36 is provided in the tip and may extend into the distal section of the sheath. In use, the slit and tip expand as a user slides an arthroscope through the tip. Thus, the slit allows the sheath to accommodate larger arthroscopes or other medical instruments.

Figure 5:
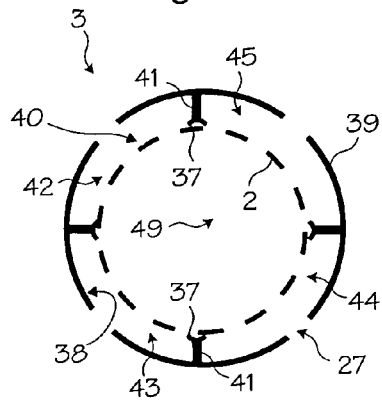
FIG. 5 shows a cross section of the distal portion of an inflow/outflow atraumatic sheath.

FIGS. 5-10 illustrate cross-sectional views of various configurations of the inflow/outflow atraumatic sheath. FIG. 5 shows a cross-sectional view of the inflow/outflow sheath 3 using the inner surface 38 of the outer wall 39 of the tube 22 with the outer surface 40 of the arthroscope 2 to form inflow and outflow outer lumens. Relatively stiff ribs 41 extending radially from the inner surface 38 of the outer wall 39 and running longitudinally along the sheath 3 form a seal with the outer surface 40 of the arthroscope, thereby creating the four outer lumens 42, 43, 44, and 45. The ends of the ribs may be provided with elastic flanges 37 or extensions to enhance the seal made between the ribs 41 and the arthroscope 2. This configuration reduces the overall size of the combined inflow/outflow sheath and arthroscope.

As depicted in FIG. 5, the arthroscope 2 is inserted into the sheath 3 through the central lumen 49. The arthroscope 2 may or may not be covered by a secondary protective sheath prior to insertion. Once inserted, the outer surface 40 of the arthroscope 2 comes in contact with the flanges or extensions of the ribs 41. A raised distinct tract, also referred to as a land, may also be used to contact the outer surface of the arthroscope 2 when the ribs 41 do not have flanges or extensions. The force of the outer surface 40 of the arthroscope 2 pushing against the ribs 41 and the rib flanges or rib extensions forms a seal between the ribs 41 and the outer surface 40 of the arthroscope 2. Outer lumens 42, 43, 44, and 45 are created by the ribs, the outer surface of the endoscope 40, and inner surface 38 of the outer wall 39 of the inflow/outflow sheath. The ribs act as longitudinal struts that prevent the sheath from collapsing as they support the sheath under compression. The ribs reduce the unsupported span of the thin outer wall in the traverse axis, further preventing the collapse of the sheath. The seals formed by the contact between the ribs 41 and the outer surface 40 of the arthroscope prevent fluids from flowing between the outer lumens 42, 43, 44, and 45. The outer lumens 42, 43, 44, and 45 facilitate the substantially continuous inflow and outflow of fluids to and from a surgical site through the holes 25 in the sheath. Check valves or gates may also be coupled to the inner surface 38 of the inflow/outflow sheath within the outer lumens 42, 43, 44, and 45 to prevent outflow fluids from flowing back towards the surgical site and to prevent inflow fluids from flowing out the proximal end of the sheath.

The inflow/outflow sheath 3 depicted in FIG. 5 typically has an outer diameter measuring about 5 to 8 millimeters when the sheath is manufactured for use with arthroscopic instruments in larger joints, though this size may vary depending on the diameter of the arthroscopic instrument. When the inflow/outflow sheath is manufactured for use with arthroscopic instruments in smaller joints, the sheath 3 has an outer diameter measuring about 2 to 5 millimeters. The outer wall 39 thickness of the inflow/outflow sheath 3 is typically 1 millimeter or less depending on the extrusion and material comprising the tube. The inflow/outflow sheath 3 can fit a range of arthroscopes +/−10% of the sheath's nominal diameter. The ribs 41 extend from the inner surface of the inflow/outflow sheath inwardly and make a tight fit when the arthroscope is inserted, or hold the arthroscope concentrically in the sheath.

A smaller outer diameter inflow/outflow sheath 3 is particularly useful in arthroscopic surgery. Due to the unique configuration, the inflow/outflow sheath 3 is able to achieve a 30% reduction in diameter when compared to multi-lumen cannula devices requiring an inner wall of a cannula contacting the outer wall of the arthroscope. Presently, arthroscopic surgical techniques use a standard three-incision technique. A first incision is made and used to insert an inflow cannula to distend the joint. The inflow cannula is used to fill the joint with a sterile fluid to expand the joint and make room for the surgeon to see and work. A second incision is made in the patient and used to insert an arthroscope to view the surgical site. A third incision is created by the surgeon to insert a specialized surgical instrument to correct the injury or abnormality. After the procedure, the joint is washed out with a stream of fluid, the instruments are removed, and the portals are closed with stitches, staples, or Steri-strips. Recently, surgeons have begun to shift to a two-incision technique during arthroscopic surgery. Surgeons use one incision for inserting the arthroscope and a second incision for inserting the specialized surgical instrument. This technique eliminates a third portal by using an arthroscope with an inflow and outflow sheath. Sheaths currently used for inflow and outflow do not, however, facilitate the continuous and simultaneous inflow and outflow of fluids to and from a surgical site with a sheath having a reduced diameter. Present sheaths only facilitate alternating inflow and outflow of fluids to the surgical site and these sheaths are of a larger diameter requiring the incision to be larger. When in use, the Applicant's inflow/outflow sheath 3 can facilitate the substantially simultaneous flow of fluids to and from a surgical site through the outer lumens 42, 43, 44, and 45 while requiring a smaller size incision. Substantially simultaneous inflow and outflow allows the surgeon to keep the surgical site clean and the field of view clear.

A unique feature of the Applicant's inflow/outflow sheath 3 is the allowance of outflow to exceed inflow in the sheath 3. Higher outflow capacity facilitates the removal of debris and bodily fluids from the surgical site. Fluid pressure supplied to the inflow/outflow sheath 3 is usually standard arthroscopic distension pressure at a pressure head of approximately 6 feet to 8 feet of water, but this may vary depending on the surgical application. Suction for use with the inflow/outflow sheath 3 ranges from approximately 0 to 250 mm/Hg depending on the sheath size and surgical application. When the inflow/outflow sheath is used in conjunction with a 5.7 mm arthroscope, the inflow of fluid to a surgical site can be performed at the rate of 800 ml/min at 6 feet of water while outflow from the surgical site can be accomplished at the rate of 850 ml/min at 21 mm/Hg suction. The higher outflow capacity is able to remove both the irrigation fluid and the additional debris and bodily fluid coming from the patient during surgery.

Figure 6:
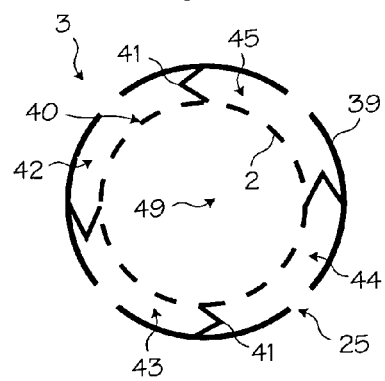
FIG. 6 shows a cross section of the distal portion of an inflow/outflow atraumatic sheath.
Figure 7:
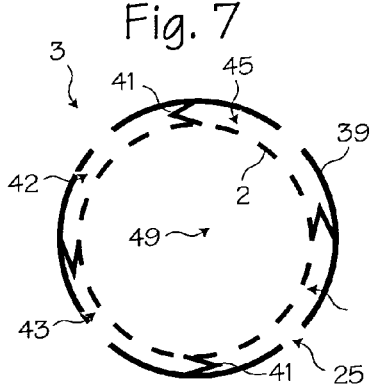
FIG. 7 shows a cross section of the distal portion of an inflow/outflow atraumatic sheath.

FIG. 6 shows an inflow/outflow atraumatic sheath 3 similar to that shown in FIG. 5. The relatively hard ribs 41 are pleated, but still form a seal with the outer wall of the arthroscope 2, thereby forming the lumens 42, 43, 44, and 45 once the arthroscope is inserted into the sheath. The sheath of FIG. 6 accommodates a variety of sizes of arthroscopes because the pleated ribs will bend to a degree necessary to accommodate larger sizes of arthroscopes, as shown in FIG. 7.

Figure 8:
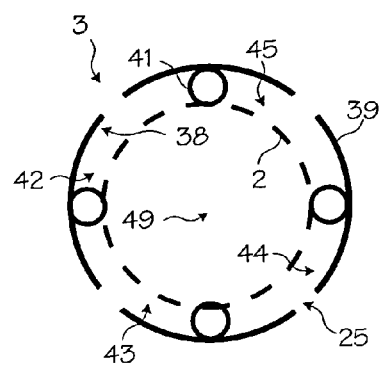
FIG. 8 shows a cross section of the distal portion of an inflow/outflow atraumatic sheath.
Figure 9:
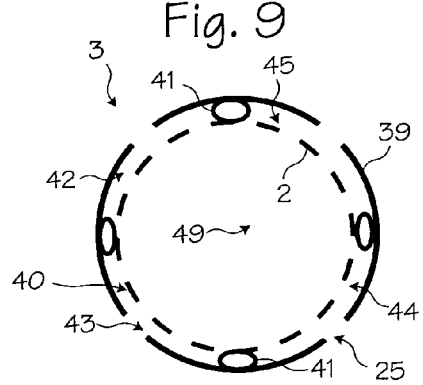
FIG. 9 shows a cross section of the distal portion of an inflow/outflow atraumatic sheath.

FIG. 8 shows an inflow/outflow atraumatic sheath 3 similar to that shown in FIG. 6. The ribs 41 of this sheath are elastic tubes that form a seal with the outer wall of the arthroscope 2, thereby forming the outer lumens 42, 43, 44, and 45 once the arthroscope is inserted into the sheath. The sheath of FIG. 8 accommodates a variety of sizes of arthroscopes since the tubes will compress to a degree necessary to accommodate larger sizes of arthroscopes, as shown in FIG. 9.

Figure 10:
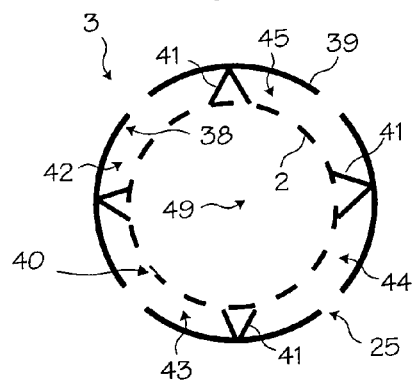
FIG. 10 shows a cross section of the distal portion of an inflow/outflow atraumatic sheath.

FIG. 10 shows a cross-section of an inflow/outflow atraumatic sheath 3 similar to that shown in FIG. 6. The ribs 41 of this sheath are V-shaped and form a seal with the outer wall of the arthroscope 2, thereby forming the outer lumens 42, 43, 44, and 45 once the arthroscope is inserted into the sheath. The sheath of FIG. 10 accommodates a variety of sizes of arthroscopes since the V-shaped ribs will compress to a degree necessary to accommodate larger sizes of arthroscopes.

Figure 11:
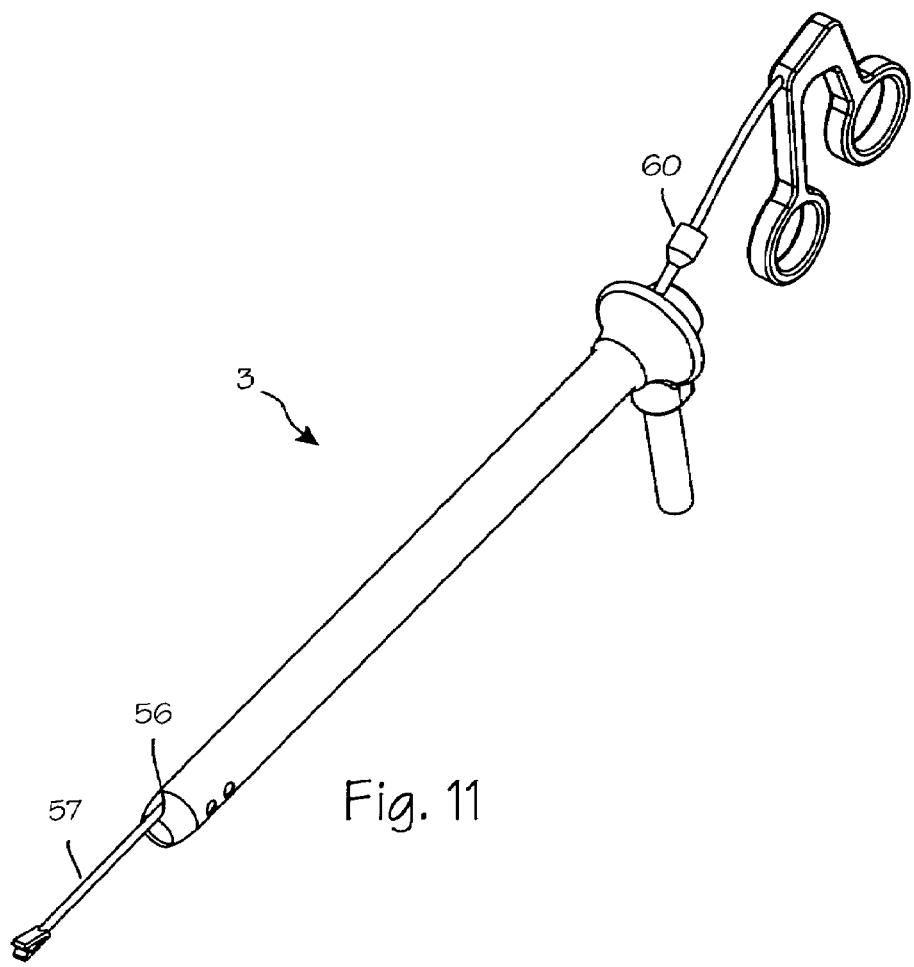
FIG. 11 depicts an inflow/outflow atraumatic sheath with a working channel.
Figure 12:
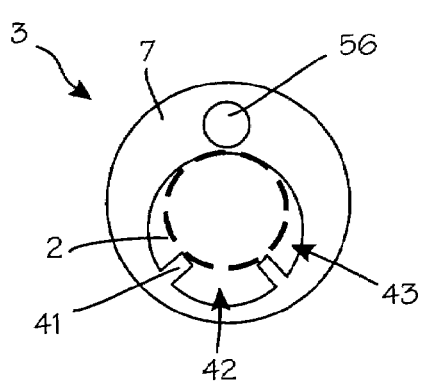
FIG. 12 shows the cross-section of an inflow/outflow atraumatic sheath with a working channel.

FIG. 11 depicts an inflow/outflow atraumatic sheath 3 with a working channel 56. A wire grasper 57 is shown disposed within the working channel. The cross-section of an inflow/outflow atraumatic sheath with a working channel is shown in FIG. 12. The atraumatic sheath 3 comprises an outer wall 39, a plurality of inward extending ribs 41 or flanges, and a working channel 56 disposed within the outer wall 39. Alternatively, the working channel may be disposed within a rib extending inwardly from an inner surface the outer wall that is sized and dimensioned to accommodate the working channel. The sheath 3 is manufactured from a sterilizable polymer. The working channel is characterized by open proximal and distal ends and a lumen running longitudinally along the atraumatic sheath 3. The proximal end of the working channel may be coupled to an adapter 60 for guiding surgical instruments into the channel when the instrument are inserted. Further, the adapter may be used for coupling the sheath to surgical instruments. The outer wall 39 of the sheath is thicker in the area where the working channel is disposed. When an arthroscopic instrument such as an arthroscope is disposed within the sheath, the inner surface 38 of the outer wall 39 of the tube 22 along with the outer surface 40 of the arthroscope 2 and the ribs form inflow and outflow outer lumens 42 and 43. The working channel lumen is so sized and dimensioned as to facilitate the insertion of a surgical instrument into the working channel for use within a surgical site.

The working channel 56 may be sized and dimensioned to accommodate a variety of surgical instruments. These surgical instruments may include a therapeutic injection catheter for injecting medicinal solutions, an ablation probe, meniscal punch, suture anchor delivery device, tissue fixation device, rotating burr, a wire grasper/basket for loose body removal, a surgical stapler or a reusable pressure sensor catheter.

Figure 13:
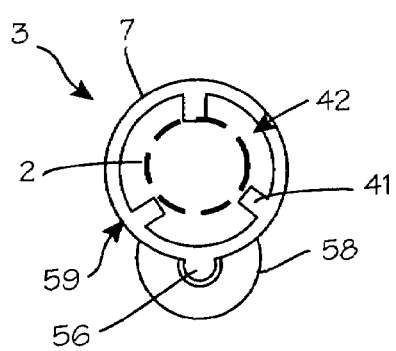
FIG. 13 shows the cross-section of an inflow/outflow atraumatic sheath with a working channel.

The inflow/outflow atraumatic sheath 3 may also be provided with a working channel 56 as depicted in FIG. 13. The working channel 56 is disposed within a raised and distinct tract such as a land 58 or rail having an arcuate cross-section and extending from the outer surface 59 of the outer wall of the atraumatic sheath. The land 58 extends longitudinally along the sheath. Fluids may also be introduced to a surgical site directly through the working channel 56. In this case, the working channel 56 is coupled at the proximal end to a fluid source containing fluids such as fluent medications, biological agents, anesthetics, diagnostic dyes, solutions, tissue adhesives and cements, or other therapeutic agents. Fluent medications are injected from the fluid source in fluid communication with the working channel using a pump or syringe, through the working channel and into the site.

Figure 14:
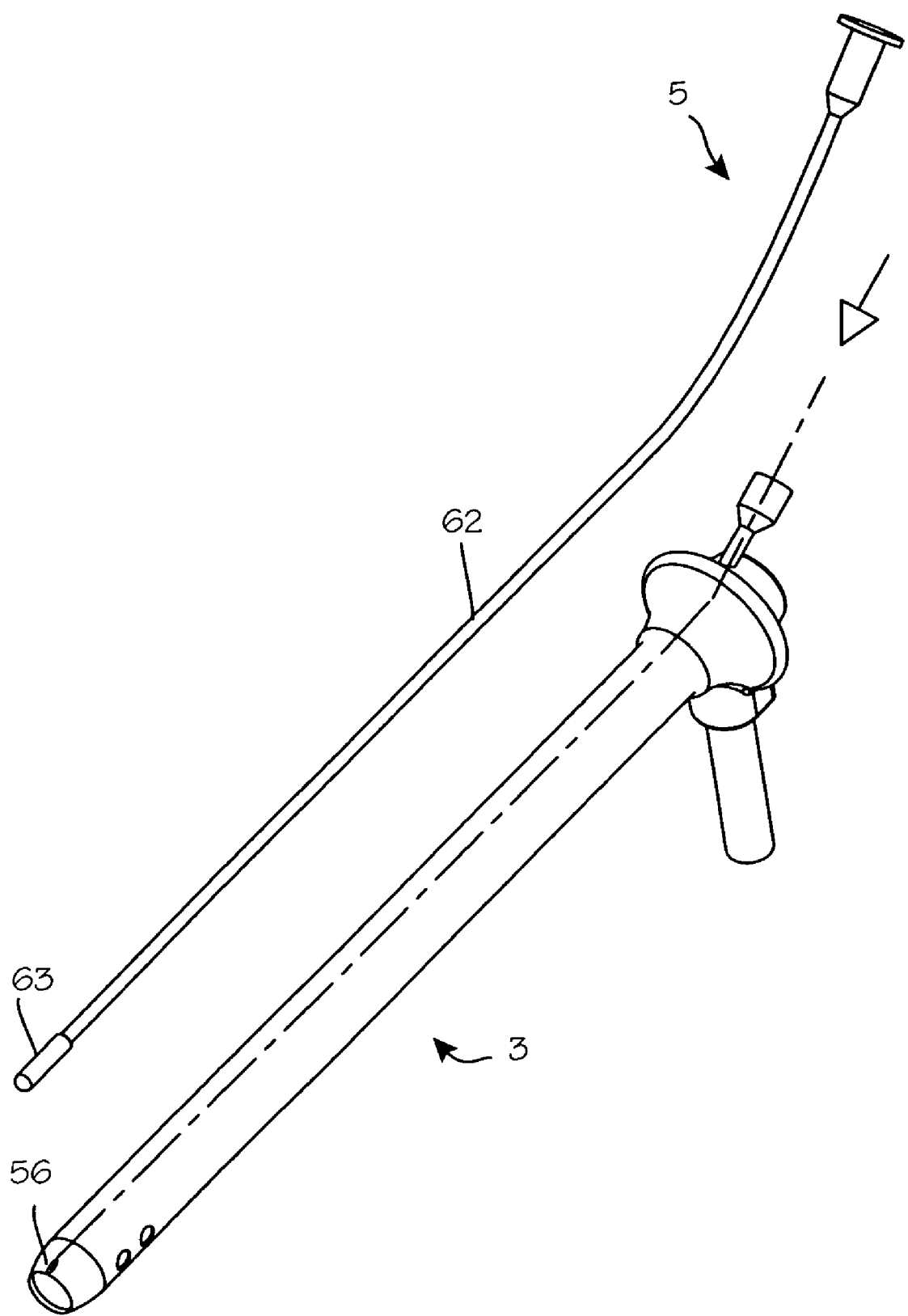
FIG. 14 depicts an inflow/outflow atraumatic sheath with a working channel and a reusable pressure sensor catheter.

FIG. 14 depicts an inflow/outflow atraumatic sheath 3 with a working channel 56 and a reusable pressure sensor catheter 61. The reusable pressure sensor catheter 61 comprises an elongated shaft 62 sized and dimensioned to fit within the working channel 56 of the atraumatic sheath. The shaft is coupled to a transducer 63 and the transducer 63 is operably coupled to a control computer within an arthroscopy suction/irrigation pump.

When in use, the reusable pressure sensor catheter 61 is inserted into the working channel 56 of the inflow/outflow sheath. The sheath along with an arthroscopic instrument and reusable pressure sensor are then inserted into a surgical site. The shaft 62 of the pressure sensor allows the transducer 63 to be placed in fluid communication with the surgical site. The control computer is then able to take measurements from the transducer and determine the pressure at the surgical site. The pressure measurements taken can be displayed to a surgeon or technician and used by the control computer within the arthroscopy inflow/outflow pump to manage the inflow and outflow of fluid to the surgical site.

Figure 15:
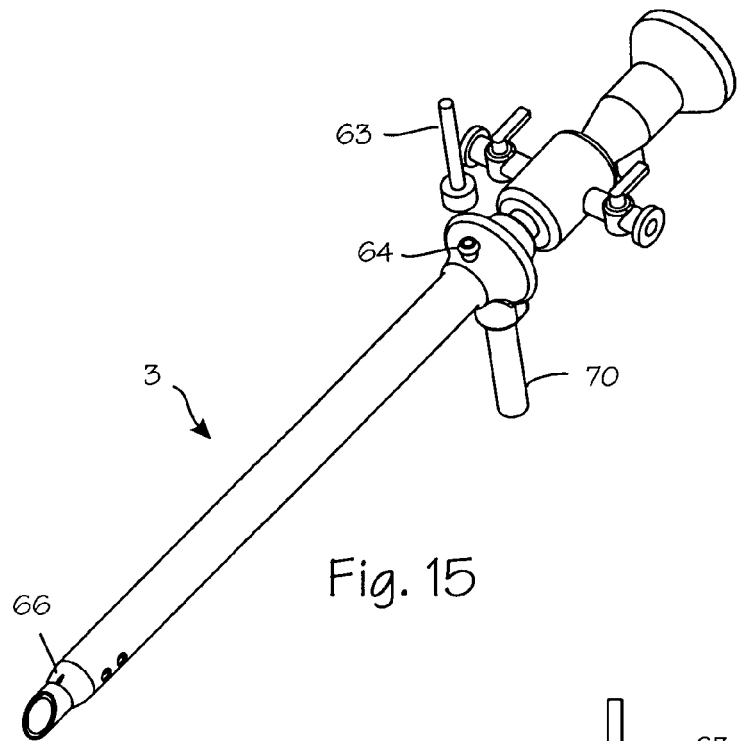
FIG. 15 depicts an inflow/outflow sheath with a pressure sensing system.
Figure 16:
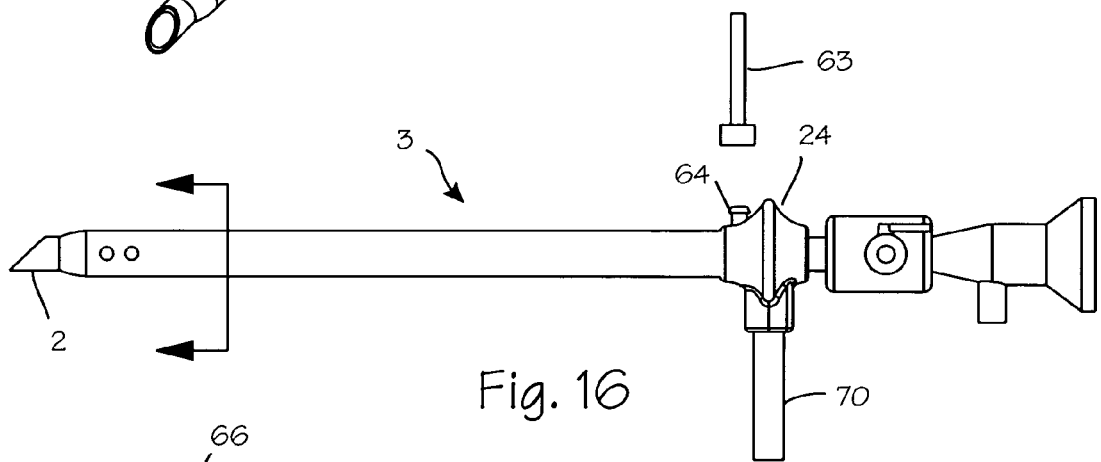
FIG. 16 depicts an inflow/outflow sheath with a pressure sensing port.
Figure 17:
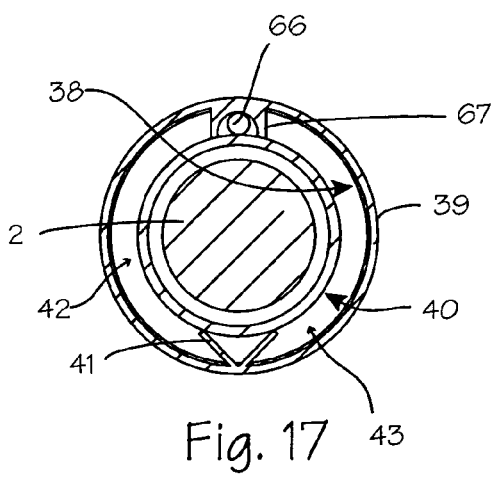
FIG. 17 depicts a cross-section of an inflow/outflow sheath with a pressure sensing port.

FIG. 15-17 depict an inflow/outflow sheath with a pressure sensing system. The inflow/out sheath is provided with a pressure sensing port 66. The pressure sensing port 66 is characterized by a lumen extending longitudinally and disposed within the outer wall of the sheath 3. Here, the pressure sensing port lumen is disposed within a land 67 protruding inwardly from the inner surface of the outer wall of the sheath. The lumen is characterized by an open distal end and proximal end allowing fluid to enter the lumen. Alternatively, the lumen may be characterized by the inner surface of the outer wall, the outer surface of the arthroscopic instrument, and ribs.

The proximal end of the sheath further comprises an elastomeric hub 24 having a fitting 64 that is adapted for coupling the hub 24 to a pressure transducer 63. The hub 24 may be coupled to the transducer 63 through a snap fitting, compression fitting, flanged fitting, flangeless fitting, threaded fitting, or mechanical device suitable coupling components in a fluid system. The hub further comprises a fluid drain tube 70 for gravity draining of fluid from the surgical site or for coupling to a vacuum source for fluid removal from the surgical site. The transducer 63 in the pressure sensing system is operably coupled to a control computer within an arthroscopy suction/irrigation pump. The transducer may be disposed anywhere between the pump and the sheath or may be disposed within the hub itself.

Figure 18:
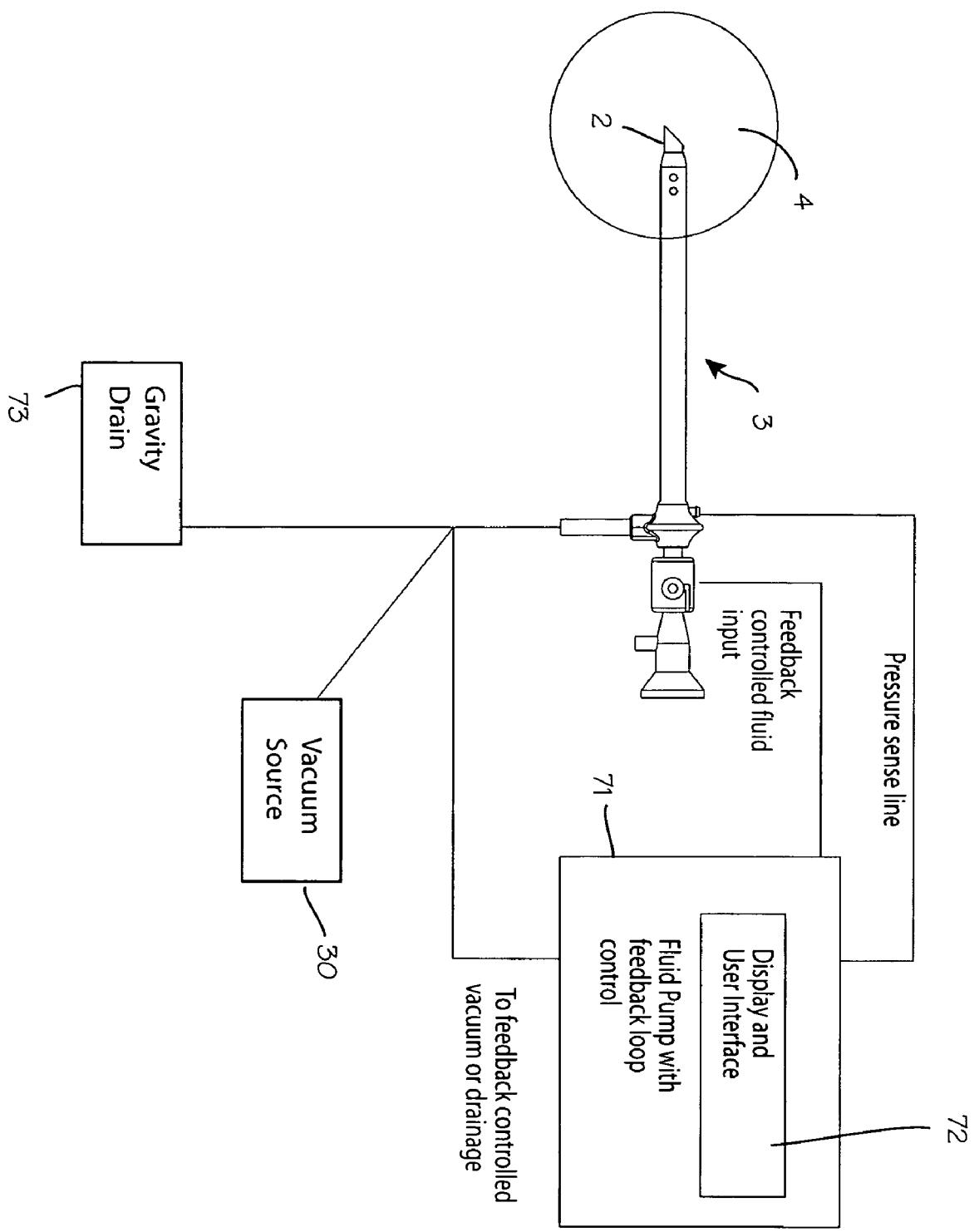
FIG. 18 illustrates an inflow/outflow sheath with a pressure sensing port in use.

When in use as depicted in FIG. 17 and 18, the pressure sensing system having a transducer 63 and control computer is coupled to the inflow/outflow sheath. An arthroscopic instrument, such as an endoscope 2, is inserted into the sheath 3 and the outer surface 40 of the arthroscopic surgical instrument is placed in contact with the ribs 41 and land 67. This contact forms seals between the land and the outer surface 40 and the ribs 41 and the outer surface 40. The outer surface 40, inner surface 38, ribs 41, and land 67 characterize outer lumens 42 and 43. The sheath, along with an arthroscopic instrument 2 disposed therein, is then inserted through a portal 12 into a surgical site such as a knee 4. The pressure sensing port in the sheath allows the transducer to be placed in fluid communication with the surgical site. The control computer 71 with feedback control is then able to take measurements from the transducer and determine the pressure at the surgical site. Pressure measurements that are taken can be displayed to a surgeon or technician by a display 72 on the arthroscopy pump and can be used by the control computer within the arthroscopy inflow/outflow pump to manage the inflow and outflow of fluid to the surgical site. More fluid can be pumped into the surgical site or fluid may be removed by a vacuum source 30 or gravity drain 73.

Figure 19:
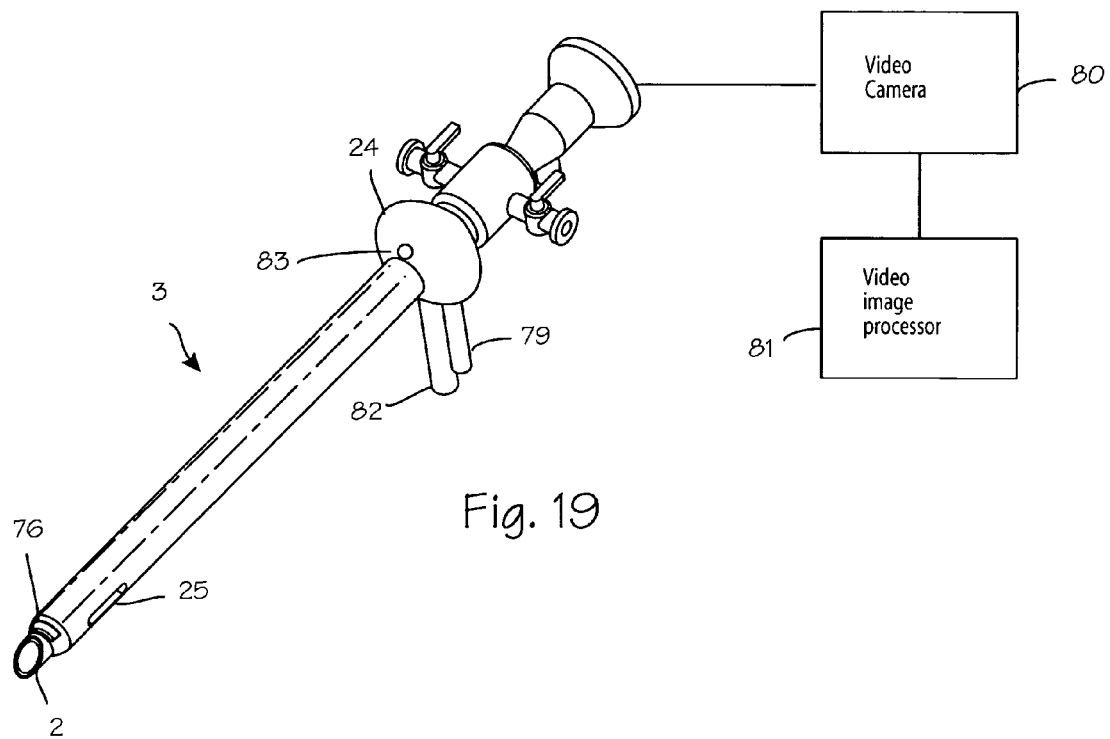
FIG. 19 depicts an inflow/outflow sheath with an illumination system.
Figure 20:
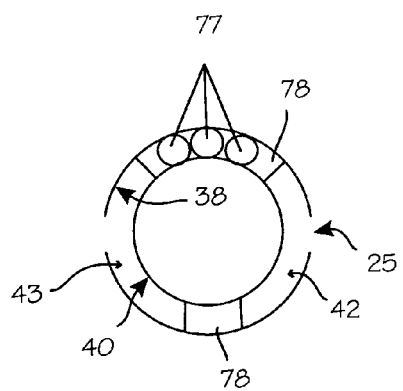
FIG. 20 illustrates a cross-section of an inflow/outflow sheath with an illumination system.

FIGS. 19 and 20 depict an inflow/outflow sheath 3 with an illumination system. The inflow/out flow sheath 3 is provided with a one or more illumination ports 76 at the distal end of the sheath 3. One or more optical fibers 77 are disposed within a land 78 or rib 41 extending inwardly from the outer wall of the inflow outflow sheath. The optical fibers extend longitudinally along the sheath and are in optical communication with the illumination port and an illumination device. The illumination device is provided within the hub 24 coupled to the proximal section of the sheath. The illumination device comprises a circuit board and a plurality of Light Emitting Diodes (LED). Photosensors may also be disposed in the illumination device when the sheath is for use with a surgical arthroscopic surgical instrument other than an arthroscope. A photosensor is an electric component that detects the presence of visible light, infrared transmission, and/or ultraviolet energy. Most photosensors comprise a semiconductor having photoconductivity that allows the electrical conductance to vary depending on the intensity of the radiation striking the material. Alternatively, the optical fibers may be coupled to an illumination device located outside the hub by an optical fiber connector coupled to the hub 24.

The LEDs in the illumination device may emit various wavelengths of light depending on the type of LED used. In some applications, an illumination device capable of emitting visible light may be used. In other applications, an illumination device emitting ultraviolet light may be used. The illumination device is in electrical communication with a power source such as a battery or power outlet. When the illumination device is provided with photosensors, the illumination device may be coupled to a control computer 81 having image analysis software and hardware as well as a display for viewing and analyzing images from a surgical site. When an endoscope is used with the sheath, as shown in FIG. 19, the endoscope is coupled to a control computer having image analysis software and hardware as well as a display for viewing and analyzing images from a surgical site.

When in use, the illumination device in the hub is coupled to a power source and control computer. When the illumination device is coupled to the sheath 3, the LEDs and/or the photosensors disposed within the housing of the illumination device are aligned with the optical fibers disposed within the outer wall, rib, or land of the inflow/outflow sheath. This alignment places the LED's and/or photosensors in optical communication with a surgical site through the illumination ports 76 when the sheath 3 is placed within a patient. Light from the LEDs is able to illuminate the surgical site. Optical sensors, when provided in the illumination device, can be used for image analysis with a camera 80 and control computer. An arthroscopic instrument, such as an endoscope 2, is inserted into the sheath 3 and the outer surface 40 of the arthroscopic surgical instrument is placed in contact with the ribs 41 and land 67. This contact forms seals between the land and the outer surface 40 and one or more ribs 41 and the outer surface 40. The outer surface 40, inner surface 38, one or more ribs 41, and land 67 characterize outer lumens 42 and 43. The lumens are in fluid communication with a fluid source and/or a vacuum source and the surgical site through one or more holes 25 in the outer wall of the sheath. Here, the holes in the sheath are slotted. The hub 24 is be adapted for coupling to a fluid source 29 and/or a vacuum source 30 through a fluid manifold 82 coupled to the hub and in fluid communication with the outer lumens.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. An atraumatic sheath comprising:
   a tube characterized by a wall, a distal section having a distal tip with a first diameter, a proximal section, an outer surface, an inner surface, an inner diameter and an outer diameter;
   wherein the inner diameter of said tube is sized and dimensioned to permit fluid flow between the inner surface of the tube and an outer surface of an arthroscopic instrument when the arthroscopic instrument is disposed within the tube;
   wherein the first diameter of the distal tip of the tube is less than an outer diameter of the arthroscopic instrument, forming a seal at the distal tip of the tube when the arthroscopic instrument is disposed within the tube;
   a plurality of ribs extending inwardly from the inner surface of the tube and running longitudinally along the tube;
   wherein said ribs further define lumens between the outer surface of the arthroscopic instrument and inner surface of the tube; and
   wherein said distal section further comprises a plurality of holes in a sidewall of the distal section of the tube, said holes in fluid communication with one or more outer lumens and a surgical site.

2. The atraumatic sheath of claim 1 wherein the proximal section further comprises a hub attachable to a fluid source and a vacuum source, said hub in fluid communication with an outer lumen.

3. The atraumatic sheath of claim 1 further comprising a working channel disposed within an inwardly projecting land extending longitudinally along the inner surface of the tube, said channel characterized by a lumen having an open distal and an open proximal end.

4. The atraumatic sheath of claim 1 further comprising a working channel disposed within an outwardly projecting land extending longitudinally along the outer surface of the tube, said channel characterized by a lumen having an open distal and an open proximal end.

5. The atraumatic sheath of claim 1 further comprising a pressure port disposed within the distal section of the sheath, said port adapted to be placed in fluid communication with a pressure transducer.

6. The atraumatic sheath of claim 1 further comprising one or more optical fibers disposed within the wall.

7. The atraumatic sheath of claim 1 further comprising one or more optical fibers disposed within an inwardly projecting land extending longitudinally along the inner surface of the tube.

8. The atraumatic sheath of claim 1 further comprising one or more optical fibers disposed within a rib.

9. A method of performing arthroscopic surgery, said method comprising the steps of:
   providing a system for performing arthroscopic surgery, said system comprising:
   a first surgical instrument suitable for performing an arthroscopic surgical procedure;
   a second surgical instrument suitable for performing an arthroscopic surgical procedure;
   an atraumatic sheath having an inner diameter sized and dimensioned to permit fluid flow between an inner surface of the sheath and an outer surface of the first surgical instrument disposed within the sheath;
   wherein the sheath has a distal tip having a first diameter which is less than an outer diameter of the first surgical instrument, forming a seal at the distal tip of the sheath when the first surgical instrument is disposed within the sheath;
   said sheath further having a plurality of ribs extending inwardly from the inner surface of said sheath and running longitudinally along said sheath;
   wherein said ribs define outer lumens between an outer surface of the first surgical instrument and the inner surface of the sheath, said lumens facilitating the inflow and outflow of fluid to and from a surgical site;

said sheath further comprising a plurality of holes in a sidewall of a distal section of the sheath said holes in fluid communication with one or more outer lumens and the surgical site;

wherein the atraumatic sheath is adapted to be removably disposed over the first surgical instrument;

placing the first surgical instrument inside the sheath;

placing the second surgical instrument within a working channel disposed within the sheath; and performing an arthroscopic surgical procedure with the system for performing arthroscopic surgery.

10. A method of performing arthroscopic surgery, said method comprising the steps of:

providing a system for performing arthroscopic surgery, said system comprising:

an arthroscopic instrument suitable for performing an arthroscopic surgical procedure;

an atraumatic sheath having an inner diameter sized and dimensioned to permit fluid flow between an inner surface of the sheath and an outer surface of the arthroscopic instrument disposed within the sheath;

wherein the sheath has a distal tip having a first diameter which is less than an outer diameter of the arthroscopic instrument, forming a seal at the distal tip of the sheath when the arthroscopic instrument is disposed within the sheath;

said sheath further having a plurality of ribs extending inwardly from the inner surface of said sheath and running longitudinally along said sheath;

wherein said ribs define outer lumens between an outer surface of the arthroscopic instrument and the inner surface of the sheath, said lumens facilitating the inflow and outflow of fluid to and from a surgical site;

said sheath further comprising a plurality of holes in a sidewall of a distal section of the sheath, said holes in fluid communication with one or more outer lumens and the surgical site;

wherein the atraumatic sheath is adapted to be removably disposed over the arthroscopic instrument;

placing the arthroscopic instrument inside the sheath;

placing a transducer in fluid communication with a pressure port disposed within the sheath; and performing an arthroscopic surgical procedure with the system for performing arthroscopic surgery.

11. The method of claim 10 further comprising the step of taking pressure measurements from an arthroscopic surgical site with the transducer.

12. The method of claim 11 further comprising the step of adjusting fluid inflow or fluid outflow to the arthroscopic surgical site based on the measurements taken by the transducer.

13. A method of performing arthroscopic surgery, said method comprising the steps of:

providing a system for performing arthroscopic surgery, said system comprising:

an arthroscopic instrument suitable for performing an arthroscopic surgical procedure;

an atraumatic sheath having an inner diameter sized and dimensioned to permit fluid flow between an inner surface of the sheath and an outer surface of the arthroscopic instrument disposed within the sheath;

wherein the sheath has a distal tip having a first diameter which is less than an outer diameter of the arthroscopic instrument, forming a seal at the distal tip of the sheath when the arthroscopic instrument is disposed within the sheath;

said sheath further having a plurality of ribs extending inwardly from the inner surface of said sheath and running longitudinally along said sheath;

wherein said ribs define outer lumens between an outer surface of the arthroscopic instrument and the inner surface of the sheath, said lumens facilitating the inflow and outflow of fluid to and from a surgical site;

said sheath further comprising a plurality of holes in a sidewall of a distal section of the sheath, said holes in fluid communication with one or more outer lumens and the surgical site;

wherein the atraumatic sheath is adapted to be removably disposed over the arthroscopic instrument;

placing the arthroscopic instrument inside the sheath;

placing a optical fiber disposed within the sheath in optical communication with an illumination device and an illumination port disposed on the distal section of the sheath; and performing an arthroscopic surgical procedure with the system for performing arthroscopic surgery.

14. A method of claim 13 further comprising the step of illuminating an arthroscopic surgical site with the illumination device.

15. A method of performing arthroscopic surgery, said method comprising the steps of:

providing a system for performing arthroscopic surgery, said system comprising:

a surgical instrument suitable for performing an arthroscopic surgical procedure;

an atraumatic sheath having an inner diameter sized and dimensioned to permit fluid flow between an inner surface of the sheath and an outer surface of the surgical instrument disposed within the sheath, said sheath comprising a working channel disposed within the sheath;

wherein the sheath has a distal tip having a first diameter which is less than an outer diameter of the surgical instrument, forming a seal at the distal tip of the sheath when the surgical instrument is disposed within the sheath;

said sheath further comprising a plurality of ribs extending inwardly from the inner surface of said sheath and running longitudinally along said sheath;

wherein said ribs define outer lumens between an outer surface of the surgical instrument and the inner surface of the sheath, said lumens facilitating the inflow and outflow of fluid to and from a surgical site;

said sheath further comprising a plurality of holes in a sidewall of a distal section of the sheath, said holes in fluid communication with one or more outer lumens and the surgical site;

wherein the atraumatic sheath is adapted to be removably disposed over the surgical instrument;

placing the surgical instrument inside the sheath;

coupling the atraumatic sheath to a first fluid source;

coupling the atraumatic sheath to a second fluid source in fluid communication with the working channel;

performing an arthroscopic surgical procedure with the system for performing arthroscopic surgery.

16. The method of claim 15 wherein the first fluid source contains an irrigating solution and the second fluid source contains a fluent medication.

17. The method of claim 15 wherein the first fluid source contains an irrigating solution and the second fluid source contains a fluid selected from the group of fluids comprising fluent medications, anesthetics, biological agents, dyes, tissue adhesives and tissue cements.

18. An atraumatic sheath comprising:
a tube characterized by a wall, a distal section, a proximal section, an outer surface, an inner surface, an inner diameter and an outer diameter;
wherein the inner diameter of said tube is sized and dimensioned to permit fluid flow between the inner surface of the tube and an outer surface of an arthroscopic instrument when the arthroscopic instrument is disposed within the tube; and
a plurality of ribs extending inwardly from the inner surface of the tube and running longitudinally along the tube;
wherein said ribs further define lumens between the outer surface of the arthroscopic instrument and inner surface of the tube;
one or more optical fibers disposed within an inwardly projecting land extending longitudinally along the inner surface of the tube.

19. An atraumatic sheath comprising:
a tube characterized by a wall, a distal section, a proximal section, an outer surface, an inner surface, an inner diameter and an outer diameter;
wherein the inner diameter of said tube is sized and dimensioned to permit fluid flow between the inner surface of the tube and an outer surface of an arthroscopic instrument when the arthroscopic instrument is disposed within the tube; and
a plurality of ribs extending inwardly from the inner surface of the tube and running longitudinally along the tube;
wherein said ribs further define lumens between the outer surface of the arthroscopic instrument and inner surface of the tube;
one or more optical fibers disposed within a rib.

* * * * *

UNITED STATES PATENT AND TRADEMARK OFFICE
CERTIFICATE OF CORRECTION

PATENT NO.         : 7,500,947 B2  Page 1 of 1
APPLICATION NO. : 11/094626
DATED               : March 10, 2009
INVENTOR(S)       : Theodore R. Kucklick and Martin Trieb It is certified that error appears in the above-identified patent and that said Letters Patent is hereby corrected as shown below:

On the Title page, Item 73

Assignee: Replace [Cannonflow, Inc.] with "Cannuflow, Inc."

Signed and Sealed this

Second Day of June, 2009

JOHN DOLL
*Acting Director of the United States Patent and Trademark Office*